US00PP31525P2

(12) United States Plant Patent
Sheehan

(10) Patent No.: US PP31,525 P2
(45) Date of Patent: Mar. 10, 2020

(54) GRAPEVINE PLANT NAMED 'SHEEGENE 103'

(50) Latin Name: *Vitis vinifera*
Varietal Denomination: Sheegene 103

(71) Applicant: Sheehan Genetics Australia PTY. Ltd., Mildura (AU)

(72) Inventor: Timothy P. Sheehan, Vancouver, WA (US)

(73) Assignee: Sheehan Genetics Australia PTY. Ltd., Mildura (AU)

( * ) Notice: Subject to any disclaimer, the term of this patent is extended or adjusted under 35 U.S.C. 154(b) by 0 days.

(21) Appl. No.: 16/350,752

(22) Filed: Jan. 2, 2019

(51) Int. Cl.
*A01H 5/08* (2018.01)
*A01H 6/88* (2018.01)

(52) U.S. Cl.
USPC ..... Plt./205

(58) Field of Classification Search
USPC ..... Plt./156, 205
See application file for complete search history.

(56) References Cited

U.S. PATENT DOCUMENTS

| | | | |
|---|---|---|---|
| PP4,787 | P | 11/1981 | Olmo |
| PP17,211 | P2 | 11/2006 | Gargiulo |
| PP17,504 | P3 | 3/2007 | Maranto |
| PP17,875 | P3 | 7/2007 | Gargiulo |
| PP18,226 | P3 | 11/2007 | Gargiulo |
| PP18,959 | P2 | 6/2008 | Sheehan |
| PP18,960 | P2 | 6/2008 | Sheehan |
| PP18,987 | P2 | 6/2008 | Sheehan |
| PP19,041 | P2 | 7/2008 | Sheehan |
| PP19,599 | P2 | 12/2008 | Maranto |
| PP19,911 | P2 | 4/2009 | Sheehan |
| PP19,912 | P2 | 4/2009 | Sheehan |
| PP20,110 | P3 | 6/2009 | Sheehan |
| PP20,236 | P3 | 8/2009 | Sheehan |
| PP20,252 | P3 | 9/2009 | Sheehan |
| PP20,281 | P3 | 9/2009 | Sheehan |
| PP20,317 | P3 | 9/2009 | Sheehan |
| PP20,753 | P3 | 2/2010 | Sheehan |
| PP21,075 | P2 | 6/2010 | Maranto |
| PP21,316 | P3 | 9/2010 | Sheehan |
| PP23,125 | P2 | 10/2012 | Sheehan |
| PP23,478 | P3 | 3/2013 | Chimenti |
| PP23,837 | P3 | 8/2013 | Sheehan |
| PP25,095 | P3 | 11/2014 | Sheehan |
| PP25,131 | P3 | 12/2014 | Sheehan |
| PP26,179 | P3 | 12/2015 | Sheehan |
| PP26,300 | P3 | 1/2016 | Lombard |
| PP28,269 | P3 | 8/2017 | Sheehan |
| PP29,129 | P2 | 3/2018 | Sheehan |
| 2008/0201809 | P1 | 8/2008 | Sheehan |
| 2013/0276181 | P1 | 10/2013 | Sheehan |
| 2016/0044845 | P1 | 2/2016 | Sheehan |

OTHER PUBLICATIONS

U.S. Appl. No. 16/350,750, filed Jan. 2, 2019, Sheehan.
U.S. Appl. No. 16/350,751, filed Jan. 2, 2019, Sheehan.
Application for Plant Breeder's Rights for Grapevine ( *Vitis vinifera*) Variety Sheegene 103, Australia, PBR No. 2019/026, filed Feb. 20, 2019.
Variety specific information as indicated in transmittal letter of Information Disclosure Statement for U.S. Appl. No. 16/350,751, filed May 8, 2019.

*Primary Examiner* — Susan McCormick Ewoldt
*Assistant Examiner* — Karen M Redden
(74) *Attorney, Agent, or Firm* — Dentons US LLP

(57) ABSTRACT

'Sheegene 103' is a new grapevine plant with novel characteristics that include large, natural loose bunches and seedless berries. The berries produced by 'Sheegene 103' are large and exhibit a datiform shape with a sweet, prominent flavor.

1 Drawing Sheet

Latin name of the genus and species of the plant claimed: *Vitis vinifera.*

Cultivar denomination: 'Sheegene 103'.

BACKGROUND OF THE INVENTION

The present invention relates to a new distinct variety of grapevine named 'Sheegene 103'. The variety originated from a hybridization performed in Mildura, Victoria, Australia during 2004 between 'Stanley Seedless' (unpatented), as the pollen parent, and 'Crimson Seedless' (unpatented), as the seed parent. Abortive seed traces were embryo cultured and the resulting plant was planted in an evaluation block during 2006. The first evaluation of fruit was performed during 2009. 'Sheegene 103' was first asexually propagated by field grafting dormant hardwood scions to rootstock in 2010 in Irymple, Victoria, Australia. Fruit from the resulting sixteen grafted 'Sheegene 103' vines was first harvested in 2014. All characteristics and distinctions remain true to form and are established and transmitted through succeeding propagations.

SUMMARY OF THE INVENTION

The following are the most outstanding and distinguishing characteristics of 'Sheegene 103'. 'Sheegene 103' produces large and naturally loose bunches. The berries produced by 'Sheegene 103' are red (5R 4/6) and exhibit a datiform shape, good evenness, and sweet, prominent flavor.

'Sheegene 103' can be distinguished from its male parent, 'Stanley Seedless', based at least upon berry color, shape, and length. 'Sheegene 103' produces red berries; whereas, 'Stanley Seedless' produces green yellow berries. The berries produced by 'Sheegene 103' exhibit a datiform shape; whereas, those produced by 'Stanley Seedless' exhibit a roundish shape. The berries produced by 'Sheegene 103' (37 mm on average) are longer than those produced by 'Stanley Seedless' (23 mm on average).

'Sheegene 103' can be distinguished from its female parent, 'Crimson Seedless', based at least upon berry size, shape, and diameter:length ratio, bunch size, bunch density, time of berry ripening, and harvest period. 'Sheegene 103' produces datiform berries with their average diameter being half their average length (18 mm diameter×37 mm length) and that weigh on average 8.5 g/berry. 'Crimson Seedless' produces oval berries with their average diameter more equal to their average length (16.6 mm diameter×22.2 mm length) and that weigh on average 4 g/berry. 'Sheegene 103' produces large, dense bunches of berries, whereas 'Crimson Seedless' produces bunches of berries exhibiting medium size and density. 'Sheegene 103' produces berries that exhibit early ripening, whereas 'Crimson Seedless' produces berries that exhibit medium to late ripening. 'Sheegene 103' is harvested in August, which is earlier than the late September to early November harvest period of 'Crimson Seedless'.

'Sheegene 103' can be distinguished from 'Sheegene 10' (U.S. Plant Pat. No. 18,959) based at least upon berry shape and color. Berries produced by 'Sheegene 103' exhibit a datiform shape and red color. Berries produced by 'Sheegene 10' exhibit a broad ellipsoid shape and dark red violet color.

'Sheegene 103' can be distinguished from 'Flame Seedless' (unpatented) based at least upon berry shape, seed formation, bunch density, and time of berry ripening. Berries produced by 'Sheegene 103' exhibit a datiform shape and comprise rudimentary seeds. Berries produced by 'Flame Seedless' exhibit a globose shape and do not comprise seeds. 'Sheegene 103' produces dense bunches of berries, whereas 'Flame Seedless' produces bunches of berries exhibiting lax to medium density. 'Sheegene 103' produces berries that exhibit early ripening, whereas 'Flame Seedless' produces berries that exhibit very early ripening.

'Sheegene 103' can be distinguished from 'Ralli Seedless' (U.S. Plant Pat. No. 9,865) based at least upon berry shape and bunch density. Berries produced by 'Sheegene 103' exhibit a datiform shape, whereas berries produced by 'Ralli Seedless' exhibit a broad ellipsoid shape. 'Sheegene 103' produces dense bunches of berries, whereas 'Ralli Seedless' produces bunches of berries exhibiting lax to medium density.

BRIEF DESCRIPTION OF THE DRAWING

'Sheegene 103' is illustrated by the accompanying photograph, which shows the form, foliage, and fruit of a 4-year-old vine grown in the field at Murcia, Spain.

The colors shown are as true as can be reasonably obtained by conventional photographic procedures.

DETAILED BOTANICAL DESCRIPTION

The following detailed description sets forth the distinctive characteristics of 'Sheegene 103'. The detailed description was obtained between March and November using 4-year-old plants grown in the field at Murcia, Spain. The color references are to the *Munsell Color Charts for Plant Tissue,* 1977 Edition by Munsell Color.

Classification:

*Family*.—Vitaceae.

*Botanical*.—*Vitis vinifera*.

*Common name*.—Grapevine.

*Cultivar name*.—'Sheegene 103'.

Plant:

*Plant habit and growth*.—Semi erect.

*Age at maturity*.—4 years old.

*Size* (*at maturity*).—Height: 225 cm. Width: 300 cm.

*Vigor*.—Medium.

*Productivity*.—Medium to high.

*Productivity*.—22,000-27,000 pounds/acre.

*Rootstock*.—Name of rootstock: '1103 Paulsen' Rootstock (unpatented). Age of rootstock at the time of grafting: one year old.

Trunk:

*Size*.—Diameter: 6.7 cm.

*Surface texture*.—Smooth.

*Bark color*.—Exterior: 2.5YR 4/4. Interior: 2.5YR 5/8.

Canes:

*Size*.—Diameter: 9 mm. Length: 200 cm.

*Surface texture*.—Mature cane: slightly ribbed. Immature cane: smooth.

*Form* (*woody shoot cross section form*).—Pith in center with diaphragm at nodes.

*Color*.—Mature: 2.5 Y 6/4 at 5 months. Immature: 5GY7/6 at 4 weeks.

*Internode length* (*upper mature sun cane*).—11.4 cm.

Time of bud burst: March 21.

Tendrils:

*Form*.—Mostly trifid.

*Size*.—Very long. Length: 40 mm. Diameter: 3 mm.

*Texture and distribution*.—Smooth, discontinuous.

*Color*.—Mature: 2.5GY 7/4 at 4 weeks. Immature: 2.5GY 7/4 at 10 days.

*Anthocyanin*.—Mature: absent. Immature: present, 10R 5/8.

Growing tips (young shoot):

*Pubescence*.—Absent.

*Color*.—2.5GY 8/8.

*Anthocyanin*.—Present, 10R 6/8.

*Shape*.—Fully open.

*Apex*.—Triangular.

Leaves:

*Shape*.—Orbicular-reniform.

*Apex*.—Pointed.

*Base*.—Rounded.

*Margin*.—Irregular teeth.

*Length of teeth on margin*.—4 to 7 mm.

*Shape of teeth on margin*.—Mixture of both sides straight and both sides convex.

*Texture* (*mature leaf*).—Upper surface: smooth, slightly bullated along primary veins. Lower surface: smooth.

*Size*.—Immature: Length: 5.4 cm at 10 days. Width: 6.9 cm at 10 days. Mature: Length: 14.3 cm at 4 weeks. Width: 19.1 cm at 4 weeks.

*Color*.—Immature leaf: Upper surface: 2.5GY 7/8, anthocyanin 10R 6/10. Lower surface: 2.5GY 8/8, anthocyanin 10 R 5/10. Mature leaf: Upper surface: 5GY 6/6. Lower surface: 5GY 6/4.

*Venation*.—Pattern: veins on upper leaf are flat; veins on lower leaf are raised. Color: Upper surface: 5GY 7/6. Lower surface: 5GY 7/6.

*Petiolar sinus*.—Mostly closed or slightly open; lyre shaped.

*Petiole*.—Length: 12.4 cm. Diameter: 4.1 mm. Color: 5GY 7/6, anthocyanin 2.5YR 6/8.

Floral cluster:

*General description and location*.—Mostly $3^{rt}$ or $4^{th}$ node; 40% without shoulders.

*Quantity of inflorescences per cluster*.—200.

*Size*.—Length: 17.5 cm. Width: 6.7 cm (hanging), 12.3 cm (spread).

*Peduncle*.—Length: 4.8 cm.

*Inflorescences*.—Hermaphroditic.

*Stamens*.—3.1 mm, mostly straight, some wavy.

*Anthers*.—Small, nondescript.

*Date of bloom*.—Start, May 3; 50%, May 8; and 100%, May 15.

*Pollen amount*.—Sparse.

*Calyptra*.—5 segments, complete separation.

*Calyptra color*.—2.5GY 6/8.

Fruit:

*Time of year of commercial harvest and shipment*.—August.

*Storability of fruit*.—20-30 days at 4° C.

*Cluster* (*primary bunches*).—General size: medium, 686 g tipped; 890 g not tipped. Length (without peduncle): 20 cm tipped; 26 cm not tipped. Width: 17.4 cm (hanging), 22.6 cm (spread). Density: medium. Peduncle: Length: 4.1 cm. Diameter: 7.7 mm. Color: 2.5GY 7/6. Number of berries per cluster: 80 tipped; 104 not tipped. Berry: Size: large (8.5 g). Diameter: 18 mm. Length: 37 mm. Shape: datiform. Uniformity: very uniform. Brix content: 8/14, 22° brix. Skin color: 5R 4/6. Pedicel: Length: 10.5 mm. Diameter: 1.9 mm. Color: 2.5 GY 7/6. Strength of attachment to berry: medium.

*Cluster* (*secondary bunches*).—General size: medium (140 g). Length (without peduncle): 79 mm. Width: 95 mm (hanging), 119 mm (spread). Density: medium. Peduncle: Length: 52 mm. Diameter: 4.3 mm. Color: 5GY 7/6. Number of berries per cluster: 40. Berry: Size: medium (5.1 g). Diameter: 17 mm. Length: 25 mm. Shape: mostly ovoid. Uniformity: medium. Brix content: 19.2° brix. Skin color: 5R 3/8. Pedicel: Length: 6.6 mm. Diameter: 1.4 mm. Color: 2.5GY 7/6. Strength of attachment to berry: medium.

Berry flesh:

*Color*.—2.5 GY 7/6.

*Juice color*.—5Y 8/2 clear.

*Juice production*.—Medium (11% juice/berry).

*Thickness of skin*.—Medium.

*Flavor*.—Neutral.

*Fragrance*.—Neutral.

*Texture*.—Firm to crisp.

*Seeds*.—Seed rudiments (average 2 per berry), 2.5YR 7/4.

*Use*.—Table.

Disease and insect resistance: The disease and insect resistance of this cultivar is typical of its species.

What is claimed is:

1. A new and *Vitis vinifera* plant called 'Sheegene 103' as shown and described herein.

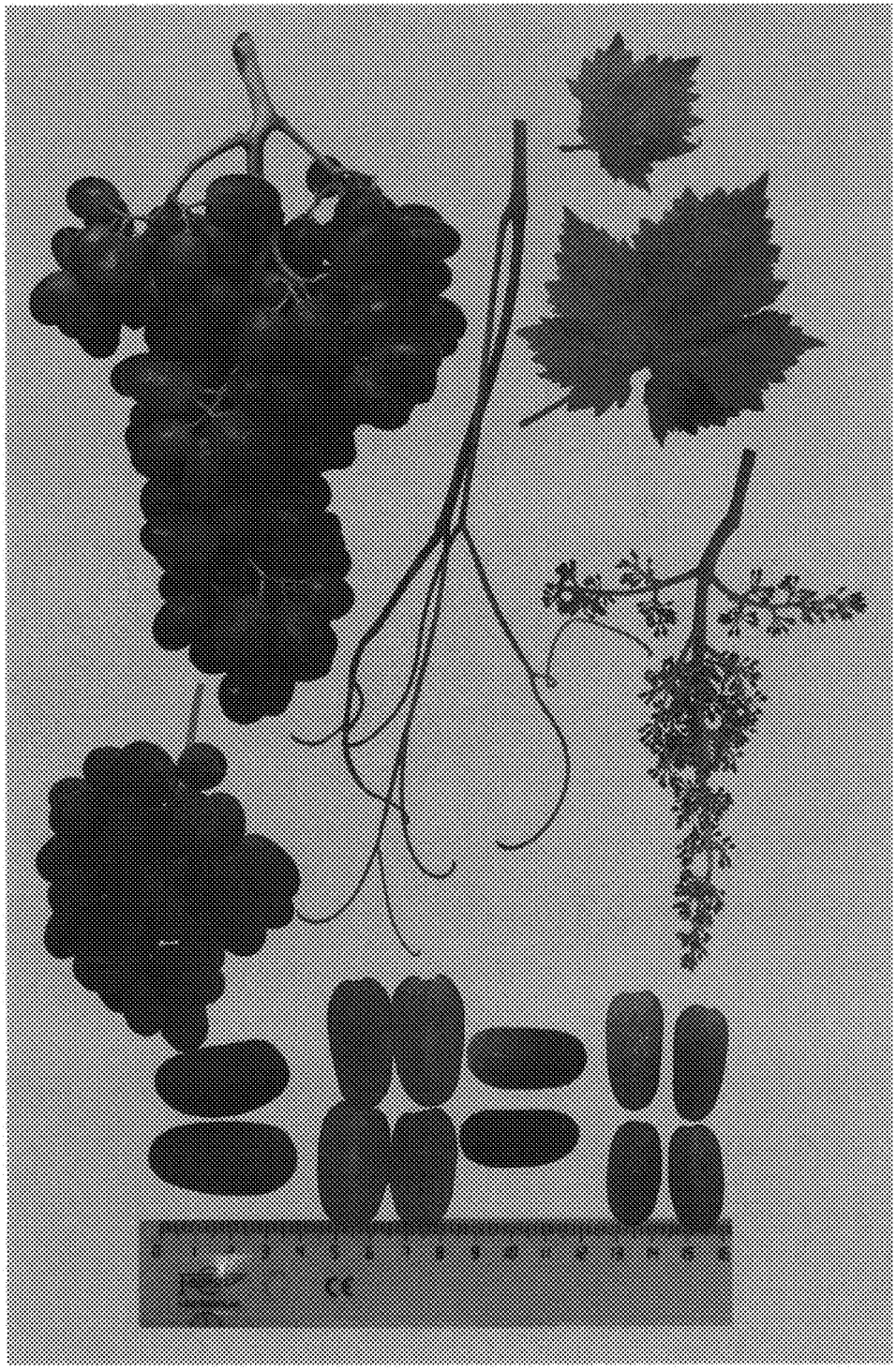

* * * * *